US011779626B2

(12) United States Patent
Baek et al.

(10) Patent No.: US 11,779,626 B2
(45) Date of Patent: Oct. 10, 2023

(54) COMPOSITION FOR ENHANCING IMMUNITY OR PREVENTING OR TREATING NEURODEGENERATIVE DISEASES BY USING GOJI BERRIES, MULBERRIES AND JUJUBES

(71) Applicant: COSMAX NS, INC., Seoul (KR)

(72) Inventors: Kwang Soo Baek, Seoul (KR); Hyunji Kim, Gyeonggi-do (KR); Su Young Choi, Gyeonggi-do (KR); Jin Hak Kim, Seoul (KR); Jae Seok Shim, Gyeonggi-do (KR); Young Min Park, Gyeonggi-do (KR); Sang Woo Kim, Gyeonggi-do (KR); Mann-Seok Yoon, Gyeonggi-do (KR); Yoon Jong Lee, Seoul (KR)

(73) Assignee: COSMAX NS, INC., Seoul (KR)

( * ) Notice: Subject to any disclaimer, the term of this patent is extended or adjusted under 35 U.S.C. 154(b) by 0 days.

(21) Appl. No.: 17/868,704

(22) Filed: Jul. 19, 2022

(65) Prior Publication Data

US 2022/0354920 A1 Nov. 10, 2022

Related U.S. Application Data

(63) Continuation of application No. 16/769,908, filed as application No. PCT/KR2018/004917 on Apr. 27, 2018, now abandoned.

(30) Foreign Application Priority Data

Jan. 5, 2018 (KR) ........................ 10-2018-0001904

(51) Int. Cl.
*A61K 36/815* (2006.01)
*A23L 33/105* (2016.01)
*A61K 36/605* (2006.01)
*A61K 36/725* (2006.01)

(52) U.S. Cl.
CPC .......... *A61K 36/815* (2013.01); *A23L 33/105* (2016.08); *A61K 36/605* (2013.01); *A61K 36/725* (2013.01); *A61K 2236/51* (2013.01)

(58) Field of Classification Search
None
See application file for complete search history.

(56) References Cited

U.S. PATENT DOCUMENTS

| | | | |
|---|---|---|---|
| 7,989,599 | B2 | 8/2011 | Suzuki et al. |
| 2008/0254143 | A1 | 10/2008 | Heuer et al. |
| 2008/0260934 | A1 | 10/2008 | Bok et al. |
| 2011/0052731 | A1 | 3/2011 | Park et al. |
| 2016/0213673 | A1 | 7/2016 | Bartos et al. |
| 2017/0361243 | A1 | 12/2017 | Kwon et al. |

FOREIGN PATENT DOCUMENTS

| | | | |
|---|---|---|---|
| CN | 101073410 | A | 11/2007 |
| CN | 104474429 | A | 4/2015 |
| CN | 104593209 | A | 5/2015 |
| CN | 106074973 | A | 11/2016 |
| CN | 106978315 | * | 7/2017 |
| CN | 106978315 | B1 | 7/2017 |
| CN | 107223979 | A | 10/2017 |
| CN | 105831637 | A | 12/2017 |
| CN | 107432473 | A | 12/2017 |
| JP | 2007-28997 | A | 2/2007 |
| KR | 10-2005-0074732 | A | 7/2005 |
| KR | 10-2006-0059631 | A | 6/2006 |
| KR | 10-0826209 | B1 | 4/2008 |
| KR | 10-2012-0007275 | A | 1/2012 |
| KR | 10-2013-0047779 | A | 5/2013 |
| KR | 20130070616 | A | * 6/2013 |
| KR | 10-2015-0012711 | A | 2/2015 |
| KR | 10-2016-0103729 | A | 9/2016 |
| KR | 10-2017-0101330 | A | 9/2017 |

OTHER PUBLICATIONS

CN106978315 translated doc (Year: 2017).*
KR20130070616A translated doc (Year: 2013).*
Ramawat et. al. (Polysaccharides Bioactivity and Biotechnology, Springer Reference, Springer International Publishing, 2015, DOI 10.1007/978-3-319-16298-0) (Year: 2015).*
USFDA (https://www.fda.gov/inspections-compliance-enforcement-and-criminal-investigations/inspection-guides/lyophilization-parenteral-793). Nov. 11, 2014 (Year: 2014).*
Vadlamudi et al. (Significance of excipients to enhance the bioavailability of poorly water-soluble drugs in oral solid dosage forms: A Review, IOP Conf. Series: Materials Science and Engineering 263 (2017) 022023). (Year: 2017).*
Amagase et al., "A review of botanical characteristics, phytochemistry, clinical relevance in efficacy and safety of *Lycium barbarum* fruit (Goji)", Food Research International, vol. 44, p. 1702-1717, (2011).
Rabiei et al., "Effects of Zizyphus jujube Extract on Memory and Learning Impairment Induced by Bilaterial Electric Lesions of the Nucleus Basalis of Meynert in Rat", Neurochem Res, 39:353-360, (2014).
USFDA, "Guide to Inspections of Lyophilization of Parenterals", Lyophilization of Parenteral (Jul. 1993), (Nov. 11, 2014).
Xixi et al., "Mechanism of Traditional Chinese and Western Medicine Research and Treatment of Senile Dementia", Asia-Pacific Traditional Medicine, vol. 11 No. 13, p. 41-44, (Jul. 2015).
Xie et al., "Recent advances in bioactive polysaccharides from *Lycium barbarum* L., *Zizyphus jujuba* Mill, *Plantago* spp., and *Morus* spp.; Structures and functionalities", Food Hydrocolloids, vol. 60, p. 148-160, (2016).

(Continued)

*Primary Examiner* — Aaron J Kosar
*Assistant Examiner* — Jacob A Boeckelman
(74) *Attorney, Agent, or Firm* — CHRISTENSEN, FONDER, DARDI & HERBERT PLLC; Diane E. Bennett; Peter S. Dardi (57) ABSTRACT

The present invention relates to a composition for enhancing immunity or a composition for preventing or ameliorating neurodegenerative diseases, both of which contain, as an active ingredient, a mixture extract of goji berries, mulberries and jujubes or an extract mixture thereof.

12 Claims, 3 Drawing Sheets

(56) References Cited

OTHER PUBLICATIONS

Zhang, "Illustrated Symptomatic Self-Massage Book", Tianjin Science and Technology Publishing House, 1st Edition, (Jul. 31, 2017).
Office Action from co-pending Korean Patent Application No. 10-2018-0001904 dated Sep. 17, 2018.
Office Action from co-pending Korean Patent Application No. 10-2018-0141534 dated Dec. 2, 2018.
International Search Report for Application No. PCT/KR2018/004917 dated Nov. 19, 2018.
Office Action from co-pending Chinese Patent Application No. 201880001387.9 dated Mar. 19, 2021.

* cited by examiner

COMPOSITION FOR ENHANCING IMMUNITY OR PREVENTING OR TREATING NEURODEGENERATIVE DISEASES BY USING GOJI BERRIES, MULBERRIES AND JUJUBES

CROSS REFERENCE TO RELATED APPLICATIONS

This application is a continuation of U.S. patent application Ser. No. 16/769,908 filed Jun. 4, 2020 to Baek et al., entitled "Composition For Enhancing Immunity Or Preventing Or Treating Neurodegenerative Diseases By Using Goji Berries, Mulberries And Jujubes", which is a national stage filing of PCT Application No. PCT/KR2018/004917 filed Apr. 27, 2018, entitled "Composition For Enhancing Immunity Or Preventing Or Treating Neurodegenerative Diseases By Using Goji Berries, Mulberries And Jujubes", which claims priority to Korean Patent Application No. 10-2018-0001904 filed Jan. 5, 2018.

BACKGROUND OF THE INVENTION

1. Field of the Invention

The present invention relates to a composition for enhancing immunity or preventing or ameliorating neurodegenerative diseases, which comprises a mixture extract of goji berries, mulberries and jujubes or an extract mixture thereof.

2. Description of the Related Art

Macrophage is a cell that regulates immune phenomena by secreting various materials in the process of phagocytosis and removal of bacteria or foreign substances and plays a pivotal role in the immune response to antigens, and involves in antigen presentation and non-specific immune response of lymphocytes, and has direct injury activity against tumor cells. In addition, it is known substances (LPS or natural products) responding to toll-like receptors (TLR) activate macrophages to produce cytokines such as IL-1, IL-6, IL-10, IL-12 and TNF-α which can regulate secondary immune responses such as defense against microbial infection, activation of macrophages for phagocytosis, and proliferation of T cells and B cells. IL-6 and TNF-α are representative cytokines induced by macrophages and are known to play a pivotal role in the inflammatory response following bacterial infection and increase their amount in inflammatory lesions. It has been reported that IL-6 is involved in the differentiation of T cells and B cells by co-operation with IL-1 and has anticancer effects. TNF-α is known to have cytotoxic and antiviral effects on certain cancer cells and play an important role in various biological reactions occurring in acute and chronic inflammatory diseases. IL-12, which is a cytokine that induces the activation of NK cells and Th1-type immune response, is known to serve to increase the reactivity to cellular foreign substances such as cancer cells.

Meanwhile, as the life of human beings is extended, neurodegenerative diseases such as cerebral infarction, stroke, amnesia, memory impairment, dementia, forgetfulness, Parkinson's disease, Alzheimer's disease, Pick's disease, Creutzfeld-Kacob disease, Huntington's disease, and amyotrophic lateral sclerosis are increasing. In neurodegenerative diseases, senile plaques (Aβ-plaques) called beta-amyloid (Aβ) accumulate in the brain tissues and neurofibrillary tangles (NFTs) appear in the brain cells, resulting in degenerative atrophy throughout the brain tissues and various associated symptoms.

Researches to show the immune enhancement efficacy through these macrophages or to prevent, treat or ameliorate neurodegenerative diseases are actively conducted, but there are no studies on goji berries, mulberries and jujubes as a raw material in relation to the symptoms.

SUMMARY OF THE INVENTION

The present invention is intended to provide a composition for preventing, treating or ameliorating neurodegenerative diseases while having an immune enhancement effect, which comprise a mixture extract of goji berries, mulberries and jujubes or an extract mixture thereof as an active ingredient.

However, the technical problem to be achieved by the present invention is not limited to the above-mentioned problem, and another problem not mentioned will be clearly understood by those skilled in the art from the following description.

The present invention provides a pharmaceutical composition for enhancing immunity comprising a mixture extract of goji berries, mulberries and jujubes or an extract mixture thereof as an active ingredient.

The weight ratio of goji berry:mulberry:jujube may be 1 to 3:1 to 3:0.5 to 1.5.

The mixture extract or the extract mixture may be lyophilized or spray dried.

The mixture extract or the extract mixture may increase macrophage-derived TNF-α expression.

The total concentration of the mixture extract or the extract mixture may be 1 μg/ml to 10 mg/ml.

In one embodiment of the present invention, there is provided a health functional food for enhancing immunity comprising a mixture extract of goji berries, mulberries and jujubes or an extract mixture thereof as an active ingredient.

In other embodiment of the present invention, there is provided a pharmaceutical composition for preventing or treating neurodegenerative diseases comprising a mixture extract of goji berries, mulberries and jujubes or an extract mixture thereof as an active ingredient.

The weight ratio of goji berry:mulberry:jujube may be 1 to 3:1 to 3:0.5 to 1.5.

The mixture extract or the extract mixture may be lyophilized or spray dried.

The mixture extract or the extract mixture may increase the ratio of mBDNF (mature BDNF) to hippocampal total BDNF.

The total concentration of the mixture extract or the extract mixture may be 1 μg/ml to 10 mg/ml.

The neurodegenerative disease may be selected from the group consisting of cerebral infarction, stroke, amnesia, memory impairment, dementia, forgetfulness, Parkinson's disease, Alzheimer's disease, Pick's disease, Creutzfeld-Kacob disease, Huntington's disease, and amyotrophic lateral sclerosis.

In another embodiment of the present invention, there is provided a health functional food for preventing or ameliorating neurodegenerative diseases comprising a mixture extract of goji berries, mulberries and jujubes or an extract mixture thereof as an active ingredient.

Effect of the Invention

The composition according to the present invention, which comprises a mixture extract of goji berries, mulberries and jujubes or an extract mixture thereof as an active ingredient, has a synergistic effect on the immune enhancement efficacy due to a combination of goji berry, mulberry and jujube and thus it can be usefully used as a pharmaceutical composition or a health functional food without cytotoxicity. In particular, when the weight ratio of goji berry, mulberry and jujube is 1 to 3:1 to 3:0.5 to 1.5, or when the mixture extract or the extract mixture is lyophilized, it is possible to further improve the immune enhancement efficacy.

In addition, the composition according to the present invention has a synergistic effect on the prevention, treatment or amelioration (especially improvement of memory) of neurodegenerative diseases due to the combination of goji berry, mulberry and jujube without cytotoxicity and thus it can be usefully used as a pharmaceutical composition or a health functional food. In particular, when the weight ratio of goji berry:mulberry:jujube is 1 to 3:1 to 3:0.5 to 1.5 or when the mixture extract or the extract mixture is spray dried, it can further improve the prevention, treatment or amelioration (especially memory improvement) of neurodegenerative diseases.

DETAILED DESCRIPTION OF THE INVENTION

The present inventors have conducted research on plant fruits in order to develop a composition for preventing, treating or ameliorating neurodegenerative diseases while having immune enhancement efficacy and found that a combination of goji berry, mulberry and jujube has the synergetic effect on the said symptoms, and thus completed the present invention.

Hereinafter, the present invention will be described in detail.

Pharmaceutical Composition for Enhancing Immunity

The present invention provides a pharmaceutical composition for enhancing immunity comprising a mixture extract of goji berries, mulberries and jujubes or an extract mixture thereof as an active ingredient.

As used herein, the term "goji berry" refers to a small red fruit of Solanaceae, which is also called a Chinese matrimony vine. A goji berry contains more than 500 times more vitamin C than oranges and has more beta-carotene than carrots, which is excellent for antioxidant activity, harmful oxygen suppression, and skin health, and high iron content, which is essential for anemia and thyroid gland. It has been known to improve digestion, protect liver cells, relieve menopausal symptoms, and reduce joint and muscle pain. A goji berry not only has anti-aging effect, but also improves sleep disorders, and is effective in preventing cardiovascular diseases. In addition, it promotes hormone secretion, helps reduce body fat and manage weight.

As used herein, the term "mulberry" refers to a mulberry fruit. It contains glucose, fructose, citric acid, malic acid, tannin and pectin, as well as vitamins (A, B1, B2, D), calcium, phosphorus and iron as a component. It is known as a tonic, and it improves the function of the intestines, especially the liver and kidneys. It relieves thirst, softens joints, degrades alcohol, and relaxes the mind, making it effective for insomnia and forgetfulness. In addition, it prevents whitening of hair, has a hematopoietic effect, is used for treatment of rheumatism, and has a reducing effect of blood sugar and cholesterol.

As used herein, the term "jujube" refers to a kind of plant fruit which has a red brown surface, an elliptical shape and a length of 1.5 to 2.5 cm, and has a sweet taste when it is red. The fruit is used as a raw food as well as a dried fruit for confectionery, cooking and medicinal purposes after drying sufficiently. In addition, a jujube is processed to use as jujube wine, jujube tea, jujube vinegar, jujube porridge. A honey jujube as a processed product is popular in China, Japan, and Europe. In oriental medicine, it is used as a diuretic, a tonic or a palliative.

As used herein, the term "mixture extract" refers to a material prepared by mixing raw materials and then extracting them simultaneously. As used herein, the term "extract mixture" refers to a material prepared by extracting raw materials individually and then mixing the extracts.

As used herein, the term "immunity enhancement" is meant to enhance or improve immune activity Immunity refers to a series of in vivo responses to protect the body from antigens that are foreign substances such as bacteria, viruses, cancer cells, and blood and tissues of other human beings or animals.

The pharmaceutical composition for enhancing immunity according to the present invention comprises a mixture extract of goji berries, mulberries and jujubes or an extract mixture thereof as an active ingredient, the mixture extract or extract mixture can increase the macrophage-derived TNF-α expression without cytotoxicity, which indicates that it has an immune enhancement efficacy.

On the other hand, in the case of the single extract of goji berries, the single extract of mulberries and the single extract of jujubes, there is only a slight increase in the macrophage-derived TNF-α expression compared to the control, which indicates that there is little immune enhancement efficacy.

The mixture extract or the extract mixture uses goji berries, mulberries and jujubes as a raw material, and the weight ratio of goji berry:mulberry:jujube is preferably 1 to 3:1 to 3:0.5 to 1.5, the weight ratio of goji berry:mulberry:jujube is more preferably 1.5 to 2.5:1.5 to 2.5:0.5 to 1.5, but is not limited thereto. In this regard, when the weight ratio of goji berry:mulberry:jujube is out of the above-described range, there is a problem in that the degree of increase in the macrophage-derived TNF-α expression is decreased compared to the control and thus the immune enhancement efficacy is reduced.

First, the mixture extract is prepared by mixing goji berries, mulberries and jujubes as a raw material and then extracting them simultaneously. Preferably, water, C1 to C4 lower alcohol or a mixture thereof is added to the mixture of goji berries, mulberries and jujubes in an amount of 2 to 20 times relative to the amount of the mixture of goji berries, mulberries and jujubes, more preferably in an amount of 3 to 10 times, but is not limited thereto. The extraction temperature is preferably 30° C. to 100° C., more preferably 70° C. to 100° C., but is not limited thereto. The extraction time is preferably 1 hour to 20 hours, more preferably 3 hours to 10 hours, but is not limited thereto. The extraction method may be any of cold extraction, ultrasonic extraction and reflux cooling extraction, but is not limited thereto. The number of extractions is preferably 1 to 5 times, more preferably 2 to 3 times, but is not limited thereto. Additionally, the mixture extract may be used by diluting, concentrating or drying after diluting or concentrating.

Next, the extract mixture is prepared by simultaneously mixing the single extract of goji berries, the single extract of mulberries and the single extract of jujubes. Preferably, water, C1 to C4 lower alcohol or a mixture thereof is added to the goji berries, the mulberries or the jujubes in an amount of 2 to 20 times relative to the amount of the goji berries, the mulberries or the jujubes, more preferably in an amount of 3 to 10 times, but is not limited thereto. The extraction temperature is preferably 30° C. to 100° C., more preferably 70° C. to 100° C., but is not limited thereto. The extraction time is preferably 1 hour to 20 hours, more preferably 3 hours to 10 hours, but is not limited thereto. The extraction method may be any of cold extraction, ultrasonic extraction and reflux cooling extraction, but is not limited thereto. The number of extractions is preferably 1 to 5 times, more preferably 2 to 3 times, but is not limited thereto. Additionally, the extract mixture may be used by diluting, concentrating or drying after diluting or concentrating.

The mixture extract or the extract mixture may be lyophilized or spray dried.

First, the lyophilization, referred to as freeze-drying, may be carried out by freezing the mixture extract or the extract mixture to be dried by rapidly lowering a temperature of a container, and then adjusting a pressure inside the container close to vacuum so that the solidified solvent contained in the mixture extract or the extract mixture is immediately sublimed with water vapor and dried. Specifically, the lyophilization may be performed for 48 hours to 168 hours at a temperature of −30° C. to −50° C.

Next, the spray drying may be carried out by spraying the mixture extract or the extract mixture to be dried in hot air to entrain fine water droplets of 1 mm or less in air stream. Specifically, the spray drying can increase dry strength by addition of dextrin.

When the mixture extract or the extract mixture is lyophilized or spray dried, there is no significant difference in the degree of cytotoxicity. However, when the mixture extract or the extract mixture is lyophilized, the degree of increase of the macrophage-derived TNF-α expression relative to the control is greatly improved compared to spray drying, which indicates that it has superior immune enhancement efficacy.

The total concentration of the mixture extract or extract mixture is preferably 1 µg/ml to 10 mg/ml, more preferably 1 µg/ml to 1 mg/ml, but is not limited thereto.

That is, even if the mixture extract or extract mixture is contained in the composition in a small concentration, it has the advantage of exhibiting sufficient immune enhancement efficacy. In this regard, if the total concentration of the mixture extract or extract mixture is less than the above-described range, there is a problem that it is difficult to exhibit sufficient immune enhancement efficacy, and if the total concentration of the mixture extract or extract mixture exceeds the above-described range, there may be toxicity concerns, including cytotoxicity.

The pharmaceutical composition for enhancing immunity according to the present invention may be formulated in the form of oral preparations such as powders, granules, tablets, capsules, suspensions, emulsions, syrups, aerosols, external preparations, suppositories, and sterile solutions for injection according to conventional methods, respectively. It may contain a suitable carrier, an excipient or a diluent which is commonly used in the manufacture of pharmaceutical compositions for formulation.

The carrier or excipient or diluent includes various compounds or mixtures including lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil and the like.

When formulated, it may be used a diluent or an excipient such as a filler, an extender, a binder, a wetting agent, a disintegrating agent, and a surfactant which is commonly used.

Solid preparations for oral administration may be prepared by mixing at least one excipient such as starch, calcium carbonate, sucrose or lactose, gelatin and the like in the mixture extract or extract mixture. In addition to simple excipients, lubricants such as magnesium stearate and talc may also be used.

Liquid preparations for oral administration may include suspensions, solvents, emulsions, and syrups, and may comprise various excipients, such as a wetting agent, a sweetener, a fragrance, and a preservative, in addition to commonly used simple diluents such as water and liquid paraffin.

Preparations for parenteral administration may include sterile aqueous solutions, non-aqueous solutions, suspensions, emulsions, lyophilized preparations, suppositories, and the like. As the non-aqueous solvent and suspending agent, propylene glycol, polyethylene glycol, vegetable oil such as olive oil, injectable ester such as ethyl oleate and the like can be used. As the base for suppositories, witepsol, macrogol, tween 61, cacao butter, laurin butter, glycerol gelatin and the like can be used.

Preferred dosages of the pharmaceutical composition for enhancing immunity according to the present invention vary depending on the condition of the patient, body weight, disease severity, drug form, route of administration and administration period, and may be appropriately selected by those skilled in the art. However, for the desired effect, it may be administered at a dose of 0.0001 to 2,000 mg/kg, preferably 0.001 to 2,000 mg/kg per day. It may be administered once a day or several times a day in a divided manner. However, the scope of the present invention is not limited by the above dosage.

The pharmaceutical composition for enhancing immunity according to the present invention can be administered to mammals such as rats, mice, livestock and humans by various routes. All modes of administration can be administered, for example, by oral, by rectal or by intravenous, intramuscular, subcutaneous, intrauterine or intracerebroventricular injection.

Health Functional Food for Enhancing Immunity

The present invention provides a health functional food for enhancing immunity comprising a mixture extract of goji berries, mulberries and jujubes or an extract mixture thereof as an active ingredient.

Since the "goji berry", "mulberry", "jujube", "mixture extract", "extract mixture" and "immunity enhancement" have been described above, duplicate descriptions will be omitted.

For the health functional food for enhancing immunity according to the present invention, when the mixture extract (or extract mixture) is used as an additive for the health functional food, it may be added as it is or used with other food or food ingredients, and can be used appropriately according to the conventional method. The amount of the active ingredient to be mixed can be appropriately determined depending on the purpose of use, such as prevention, health or treatment.

Formulations of health functional food may be in the form of powders, granules, pills, tablets, capsules, as well as in the form of general foods or beverages.

There is no particular restriction in the kind of the food. Examples of the food include meat, sausage, bread, chocolate, candy, snacks, confectionery, pizza, ramen, other noodles, gum, a dairy product including ice cream, various soups, beverages, tea, drinks, alcoholic beverages and vitamin complexes, etc. and may include all foods in a conventional sense.

Generally, the mixture extract (or extract mixture) may be added in an amount of 15 parts by weight or less, preferably 10 parts by weight or less, based on 100 parts by weight of the raw material. However, in the case of long-term intake for the purpose of health and hygiene or for health control, the amount may be less than the above range. Also, in the present invention, since there is no problem of safety in terms of using natural products, the amount may be more than the above range.

The beverage of the health functional food according to the present invention may contain various flavors or natural carbohydrates and the like as an additional ingredient as in general beverages. The above-described natural carbohydrates may be monosaccharides such as glucose and fructose, disaccharides such as maltose and sucrose, polysaccharides such as dextrin and cyclodextrin, and sugar alcohols such as xylitol, sorbitol, and erythritol. As the sweetener, natural sweeteners such as thaumatin and stevia extract, synthetic sweeteners such as saccharin and aspartame, and the like can be used. The amount of the natural carbohydrate may be about 0.01 to 0.04 g, preferably about 0.02 to 0.03 g per 100 mL of the beverage according to the present invention.

In addition, the health functional food for enhancing immunity according to the present invention may contain various nutrients, vitamins, electrolytes, flavoring agents, coloring agents, pectic acid and salts thereof, alginic acid and salts thereof, organic acids, protective colloid thickeners, pH regulators, stabilizers, preservatives, glycerin, alcohols and carbonating agents used in carbonated drinks. In addition, the composition for enhancing immunity of the present invention may contain fruit flesh for production of natural fruit juice, fruit juice beverage and vegetable beverage. These ingredients can be used alone or in combination. The ratio of such additives is not limited, but it is generally selected from the range of 0.01 to 0.1 parts by weight relative to 100 parts by weight of the dietary supplement of the present invention.

Therefore, the composition according to the present invention comprises a mixture extract of goji berries, mulberries and jujubes or an extract mixture thereof as an active ingredient and has a synergistic effect on immune enhancement efficacy due to the combination of goji berry, mulberry and jujube without cytotoxicity and thus can be usefully used as a pharmaceutical composition or a dietary supplement. In particular, when the weight ratio of goji berry:mulberry:jujube is 1 to 3:1 to 3:0.5 to 1.5 or when the mixture extract or the extract mixture is lyophilized, it is possible to further improve the immune enhancement efficacy.

In addition, the composition according to the present invention has a synergistic effect on preventing, treating or ameliorating (especially, improving memory) neurodegenerative diseases due to the combination of goji berry, mulberry and jujube without cytotoxicity and thus can be usefully used as a pharmaceutical composition or a health functional food. In particular, when the weight ratio of goji berry:mulberry:jujube is 1 to 3:1 to 3:0.5 to 1.5 or when the mixture extract or the extract mixture is spray dried, it is possible to further improve the prevention, treatment or amelioration (especially, improvement of memory) of neurodegenerative diseases.

Pharmaceutical Composition for Preventing and Treating Neurodegenerative Diseases The present invention provides a pharmaceutical composition for preventing and treating neurodegenerative diseases comprising a mixture extract of goji berries, mulberries and jujubes or an extract mixture thereof as an active ingredient.

Since the "goji berry", "mulberry", "jujube", "mixture extract" and "extract mixture" have been described above, duplicate descriptions will be omitted.

As used herein, the term "neurodegenerative disease" refers to at least one selected from the group consisting of cerebral infarction, stroke, amnesia, memory impairment, dementia, forgetfulness, Parkinson's disease, Alzheimer's disease, Pick's disease, Creutzfeld-Kacob disease, Huntington's disease, and amyotrophic lateral sclerosis.

The pharmaceutical composition for preventing or treating neurodegenerative diseases according to the present invention comprises a mixture extract of goji berries, mulberries and jujubes or an extract mixture thereof as an active ingredient, wherein the mixture extract or extract mixture can increase the ratio of mBDNF (mature BDNF) to hippocampal total BDNF without cytotoxicity, which indicates that it is possible to prevent, treat or ameliorate neurodegenerative diseases.

On the other hand, in the case of the single extract of goji berries, the single extract of mulberries and the single extract of jujubes, there is only a slight increase in the ratio of mBDNF (mature BDNF) to hippocampal total BDNF compared to the control, which indicates that it is not possible to effectively prevent, treat or ameliorate neurodegenerative diseases.

The mixture extract or the extract mixture uses goji berries mulberries and jujubes as a raw material, and the weight ratio of goji berry:mulberry:jujube is preferably 1 to 3:1 to 3:0.5 to 1.5, the weight ratio of goji berry:mulberry:jujube is more preferably 1.5 to 2.5:1.5 to 2.5:0.5 to 1.5, but is not limited thereto. In this regard, when the weight ratio of goji berry:mulberry:jujube is out of the above-described range, there is a problem in that the ratio of mBDNF (mature BDNF) to hippocampal total BDNF is decreased compared to the control and thus it is not possible to effectively prevent, treat or ameliorate neurodegenerative diseases.

First, the mixture extract is prepared by mixing goji berries, mulberries and jujubes as a raw material and then extracting them simultaneously. Preferably, water, C1 to C4 lower alcohol or a mixture thereof is added to the mixture of goji berries, mulberries and jujubes in an amount of 2 to 20 times relative to the amount of the mixture of goji berries, mulberries and jujubes, more preferably in an amount of 3 to 10 times, but is not limited thereto. The extraction temperature is preferably 30° C. to 100° C., more preferably 70° C. to 100° C., but is not limited thereto. The extraction time is preferably 1 hour to 20 hours, more preferably 3 hours to 10 hours, but is not limited thereto. The extraction method may be any of cold extraction, ultrasonic extraction and reflux cooling extraction, but is not limited thereto. The number of extractions is preferably 1 to 5 times, more preferably 2 to 3 times, but is not limited thereto. Additionally, the mixture extract may be used by diluting, concentrating or drying after diluting or concentrating.

Next, the extract mixture is prepared by simultaneously mixing the single extract of goji berries, the single extract of mulberries and the single extract of jujubes. Preferably, water, C1 to C4 lower alcohol or a mixture thereof is added to the goji berries, the mulberries or the jujubes in an amount of 2 to 20 times relative to the amount of the goji berries, the mulberries or the jujubes, more preferably in an amount of 3 to 10 times, but is not limited thereto. The extraction temperature is preferably 30° C. to 100° C., more preferably 70° C. to 100° C., but is not limited thereto. The extraction time is preferably 1 hour to 20 hours, more preferably 3 hours to 10 hours, but is not limited thereto. The extraction method may be any of cold extraction, ultrasonic extraction and reflux cooling extraction, but is not limited thereto. The number of extractions is preferably 1 to 5 times, more preferably 2 to 3 times, but is not limited thereto. Additionally, the extract mixture may be used by diluting, concentrating or drying after diluting or concentrating.

The mixture extract or the extract mixture may be lyophilized or spray dried.

First, the lyophilization, referred to as freeze-drying, may be carried out by freezing the mixture extract or the extract mixture to be dried by rapidly lowering a temperature of a container, and then adjusting a pressure inside the container close to vacuum so that the solidified solvent contained in the mixture extract or the extract mixture is immediately sublimed with water vapor and dried. Specifically, the lyophilization may be performed for 48 hours to 168 hours at a temperature of −30° C. to −50° C.

Next, the spray drying may be carried out by spraying the mixture extract or the extract mixture to be dried in hot air to entrain fine water droplets of 1 mm or less in air stream. Specifically, the spray drying can increase dry strength by addition of dextrin.

When the mixture extract or the extract mixture is lyophilized or spray dried, there is no significant difference in the degree of cytotoxicity. However, when the mixture extract or the extract mixture is spray dried, the ratio of mBDNF (mature BDNF) to hippocampal total BDNF relative to the control is greatly improved compared to lyophilizing, which indicates that it is possible to effectively prevent, treat or ameliorate neurodegenerative diseases.

The total concentration of the mixture extract or extract mixture is preferably 1 μg/ml to 10 mg/ml, more preferably 1 μg/ml to 1 mg/ml, but is not limited thereto. That is, even if the mixture extract or extract mixture is contained in the composition in a small concentration, it has the advantage of sufficiently preventing, treating or ameliorating neurodegenerative diseases. In this regard, if the total concentration of the mixture extract or extract mixture is less than the above-described range, there is a problem that it does not sufficiently prevent, treat or ameliorate neurodegenerative diseases, and if the total concentration of the mixture extract or extract mixture exceeds the above-described range, there may be toxicity concerns, including cytotoxicity.

Details regarding the formulation, effective amount, and administration method of the pharmaceutical composition for preventing or ameliorating neurodegenerative diseases according to the present invention can be applied similarly as described in the pharmaceutical composition for enhancing immunity.

Health Functional Food for Preventing or Ameliorating Neurodegenerative Diseases The present invention provides a health functional food for preventing or ameliorating neurodegenerative diseases comprising a mixture extract of goji berries, mulberries and jujubes or an extract mixture thereof as an active ingredient.

Since the "goji berry", "mulberry", "jujube", "mixture extract", "extract mixture" and "neurodegenerative disease" have been described above, duplicate descriptions will be omitted.

Meanwhile, the amelioration of the neurodegenerative diseases may mean the improvement of memory.

Details regarding the formulation, effective amount, and administration method of the dietary supplement for preventing or ameliorating neurodegenerative diseases according to the present invention can be applied similarly as described in the health functional food for enhancing immunity.

Therefore, the composition according to the present invention comprises a mixture extract of goji berries, mulberries and jujubes or an extract mixture thereof as an active ingredient and has a synergistic effect on immune enhancement efficacy due to the combination of goji berry, mulberry and jujube without cytotoxicity and thus can be usefully used as a pharmaceutical composition or a health functional food. In particular, when the weight ratio of goji berry:mulberry:jujube is 1 to 3:1 to 3:0.5 to 1.5 or when the mixture extract or the extract mixture is lyophilized, it is possible to further improve the immune enhancement efficacy.

In addition, the composition according to the present invention has a synergistic effect on preventing, treating or ameliorating (especially, improving memory) neurodegenerative diseases due to the combination of goji berry, mulberry and jujube without cytotoxicity and thus can be usefully used as a pharmaceutical composition or a health functional food. In particular, when the weight ratio of goji berry:mulberry:jujube is 1 to 3:1 to 3:0.5 to 1.5 or when the mixture extract or the extract mixture is spray dried, it is possible to further improve the prevention, treatment or amelioration (especially, improvement of memory) of neurodegenerative diseases.

Hereinafter, preferred examples are provided to help understanding the present invention. However, the following examples are merely provided to more easily understand the present invention, and the contents of the present invention are not limited by the following examples.

EXAMPLES

Example 1

About 40 g of goji berries (origin: China), about 40 g of mulberries (origin: Pakistan), and about 20 g of jujubes (origin: Korea) were mixed to prepare a mixture. The prepared mixture was mixed with 10 (v/w) times water. The mixture was extracted under reflux at 95° C. for 4 hours, filtered under reduced pressure, and concentrated in a rotary vacuum concentrator to prepare a mixture extract. Then, it was lyophilized for 72 hours at −40° C.

Example 2

About 40 g of goji berries (origin: China), about 40 g of mulberries (origin: Pakistan), and about 20 g of jujubes (origin: Korea) were mixed to prepare a mixture. The prepared mixture was mixed with 10 (v/w) times water. The mixture was extracted under reflux at 95° C. for 4 hours, filtered under reduced pressure, and concentrated in a rotary vacuum concentrator to prepare a mixture extract. Then, it was mixed with 50% by weight of dextrin and spray dried.

Comparative Example 1

Goji berries (origin: China) were mixed with 10 (v/w) times water, and the mixture was extracted under reflux for 4 hours at 95° C. Thereafter, it was filtered under reduced pressure, and concentrated in a rotary vacuum concentrator to prepare a single extract. Then, it was mixed with 50% by weight of dextrin and spray dried.

Comparative Example 2

Mulberries (origin: Pakistan) were mixed with 10 (v/w) times water, and the mixture was extracted under reflux for 4 hours at 95° C. Thereafter, it was filtered under reduced pressure, and concentrated in a rotary vacuum concentrator to prepare a single extract. Then, it was mixed with 50% by weight of dextrin and spray dried.

Comparative Example 3

Jujubes (origin: Korea) were mixed with 10 (v/w) times water, and the mixture was extracted under reflux for 4 hours at 95° C. Thereafter, it was filtered under reduced pressure, and concentrated in a rotary vacuum concentrator to prepare a single extract. Then, it was mixed with 50% by weight of dextrin and spray dried.

Experimental Example 1: Evaluation of Cytotoxicity

Cell viability was measured in order to evaluate the cytotoxicity of the composition prepared in Examples 1 and 2 and Comparative Examples 1 to 3.

First, mouse macrophage cell line RAW264.7 cells were cultured at a density of 70-80% in a 100 mm cell culture dish using RPMI 1640 medium containing penicillin (100 IU/ml) and streptomycin (100 μg/ml) and 10% FBS.

Then, it was analyzed using MTT (3-[4,5-dimethylthiazol-2-yl]-2,5-diphenyltetrazolium bromide) assay. The cultured mouse macrophage cell line RAW264.7 cells were adjusted to a concentration of $1\times10^6$ cell/ml using RPMI 1640 medium, and then inoculated into a 96 well plate and precultured at 5% $CO_2$ and 37° C. for 18 hours. Thereafter, the medium was removed, and culture was performed in the medium treated with the test material at a concentration shown in the figures. After 24 hours, 10 μl MTT solution (stock concentration: 5 mg/ml) was added to induce an additional reaction for 3 hours. 100 μl DMSO was additionally added to each well to terminate the reaction and dissolve formazan crystals. Cell viability was measured by calculating the amount of MTT reduced to formazan through the OD value obtained by measuring the absorbance at 570 nm, and the results are shown in FIG. 1.

Figure 1:
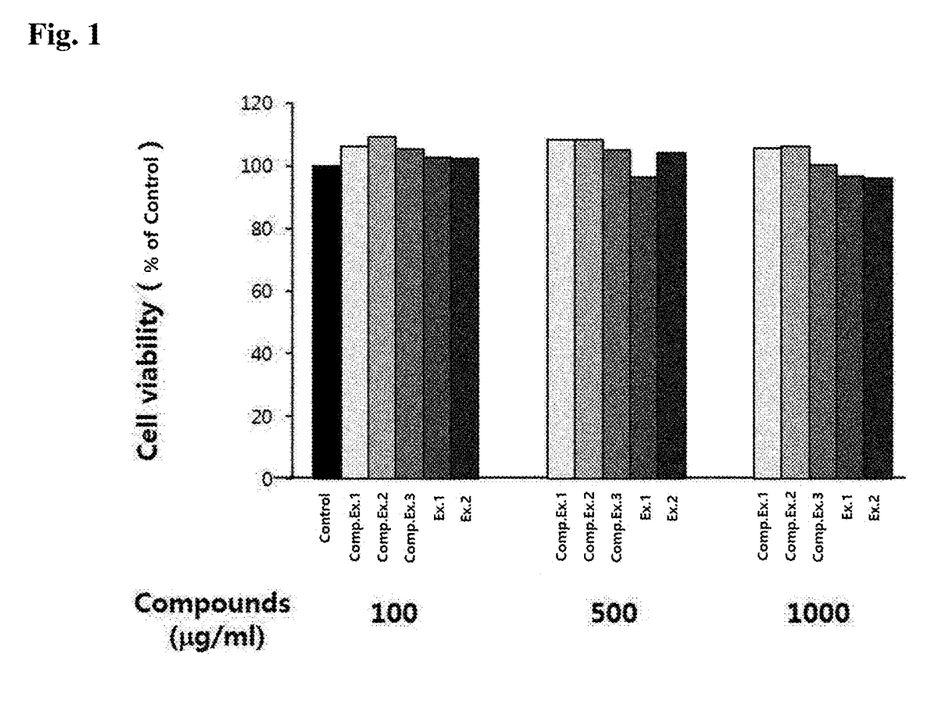
FIG. 1 is a graph showing the results of evaluating the cytotoxicity of the compositions prepared in Examples 1 and 2 and Comparative Examples 1 to 3.

As shown in FIG. 1, the cell viability in the case of treating with the compositions prepared in Examples 1 and 2 and Comparative Examples 1 to 3 was found to be 80% or more, indicating that there is no cytotoxicity.

Experimental Example 2: Determination of Macrophage-Derived TNF-α Expression

In order to compare the immune enhancement efficacy of the compositions prepared in Examples 1 and 2 and Comparative Examples 1 to 3, the TNF-α expression was measured.

First, the cultured mouse macrophage cell line RAW264.7 cells in Experimental Example 1 were adjusted to a concentration of $1\times10^6$ cell/ml using RPMI 1640 medium, and then inoculated into a 96 well plate and precultured at 5% $CO_2$ and 37° C. for 18 hours. Thereafter, the medium was removed, and culture was performed in the medium treated with the test material at a concentration shown in the figures. After 24 hours, the supernatant was transferred to another 96 well plate by 100 μl, and measured the macrophage-derived TNF-α expression by using an enzyme-linked immunosorbent assay (ELISA) kit of R&D systems according to the manufacturer's instructions, and the results are shown in FIG. 2.

Figure 2:
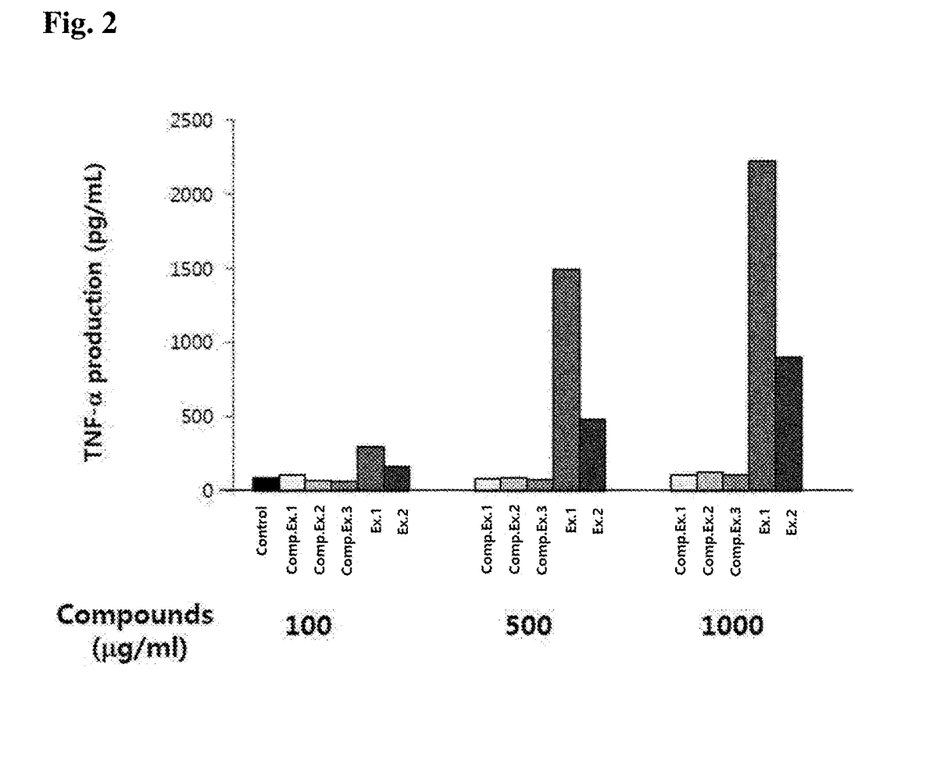
FIG. 2 is a graph comparing the measurement results of macrophage-derived TNF-α expression of the compositions prepared in Examples 1 and 2 and Comparative Examples 1 to 3.

As shown in FIG. 2, the macrophage-derived TNF-α expression in the case of treating with the compositions prepared in Examples 1 and 2 was found to be 100.00 pg/ml or more, indicating that the immune enhancement efficacy is excellent. In particular, the macrophage-derived TNF-α expression in the case of treating with the composition (a weight ratio of goji berry:mulberry:jujube=2:2:1) prepared in Examples 1 and 2 was found to be 160.00 pg/ml or more, indicating that the immune enhancement efficacy is significantly excellent.

In this regard, when comparing the immune enhancement efficacy of the compositions prepared in Examples 1 and 2 to the immune enhancement efficacy of the compositions prepared in Comparative Examples 1 to 3 having the corresponding concentration of goji berry, mulberry and jujube, the macrophage-derived TNF-α expression in the case of treating with the compositions prepared in Examples 1 and 2 was found to be improved compared to the case of treating with the compositions prepared in Comparative Examples 1 to 3, indicating that the combination of goji berry, mulberry and jujube have a synergistic effect on the immune enhancement efficacy.

Experimental Example 3: Measurement of Ratio of mBDNF to Hippocampal Total BDNF

In order to compare the efficacy of preventing, treating or ameliorating neurodegenerative diseases of the compositions prepared in Examples 1 and 2 and Comparative Examples 1 to 3, total BDNF expression and mature BDNF expression were measured.

First, the cultured mouse hippocampal cell line HT22 cells in Experimental Example 1 were adjusted to a concentration of $1\times10^4$ cell/ml using DMEM medium, and then inoculated into a 96 well plate and preincubated at 5% $CO_2$ and 37° C. for 18 hours. Thereafter, the medium was removed, and culture was performed in the medium treated with the test material at a concentration shown in the figures. After 24 hours, the supernatant was transferred to another 96 well plate by 100 μl, and measured a concentration of total BDNF and a concentration of mature BDNF by using an enzyme-linked immunosorbent assay (ELISA) kit of R&D systems and calculated a ratio of mature BDNF to total BDNF, and the results are shown in FIG. 3.

Figure 3:
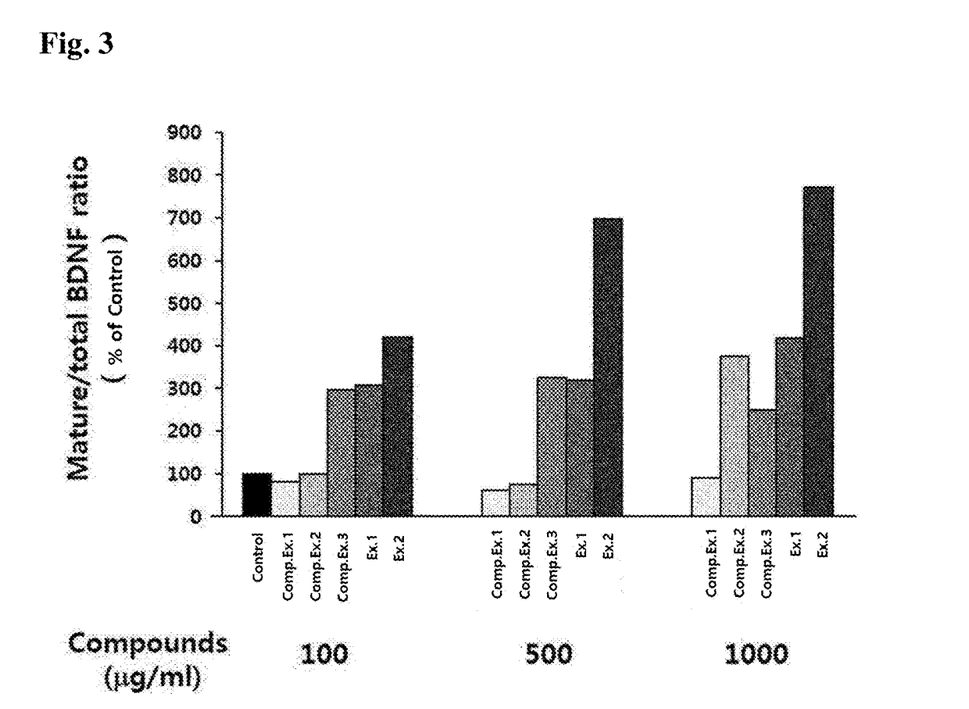
FIG. 3 is a graph comparing the measurement results of the ratio of mBDNF (mature BDNF) to hippocampal total BDNF of the compositions prepared in Examples 1 and 2 and Comparative Examples 1 to 3.

As shown in FIG. 3, the ratio of mBDNF to total BDNF in the case of treating with the compositions prepared in Examples 1 and 2 was found to be 300% or more compared with the control, indicating that the efficacy of preventing, treating or ameliorating neurodegenerative diseases is excellent.

In this regard, when comparing the efficacy of preventing, treating or ameliorating neurodegenerative diseases of the compositions prepared in Examples 1 and 2 to the efficacy of preventing, treating or ameliorating neurodegenerative diseases of the compositions prepared in Comparative Examples 1 to 3 having the corresponding concentration of goji berry, mulberry and jujube, the ratio of mBDNF to hippocampal total BDNF in the case of treating with the compositions prepared in Examples 1 and 2 is improved compared to the case of treating with the compositions prepared in Comparative Examples 1 to 3, indicating that the combination of goji berry, mulberry and jujube have a synergistic effect on the efficacy of preventing, treating or ameliorating neurodegenerative diseases.

In the following, preparative examples of a composition containing the mixture extract (or extract mixture) of the present invention will be described. However, it is not intended to be limited thereto, but is intended to be described in detail.

Preparative Example 1: Preparation of Powder

| Mixture extract (or extract mixture) | 20 mg |
|---|---|
| Lactose hydrate | 100 mg |
| Talc | 10 mg |

The above ingredients were mixed and then filled in an airtight fabric to prepare a powder.

Preparative Example 2: Preparation of Tablet

| Mixture extract (or extract mixture) | 10 mg |
|---|---|
| Corn starch | 100 mg |
| Lactose hydrate | 100 mg |
| Stearate magnesium | 2 mg |

The above ingredients were mixed and then compressed according to a conventional preparation method of tablets to prepare a tablet.

Preparative Example 3: Preparation of Capsule

| Mixture extract (or extract mixture) | 10 mg |
|---|---|
| Microcrystalline cellulose | 3 mg |
| Lactose hydrate | 14.8 mg |
| Stearate magnesium | 0.2 mg |

The above ingredients were mixed and then filled in a gelatin capsule according to a conventional preparation method of capsules to prepare a capsule.

Preparative Example 4: Preparation of Injection Formulation

| Mixture extract (or extract mixture) | 10 mg |
|---|---|
| Mannitol | 180 mg |
| Sterile distilled water for injection | 2974 mg |
| Sodium monohydrogen phosphate | 26 mg |

The above ingredients were mixed and then filled in an ampoule in the above-described content of ingredients per ampoule (2 mL) according to a conventional preparation method of injections to prepare an injection formulation.

Preparative Example 5: Preparation of Liquid Formulation

| Mixture extract (or extract mixture) | 10 mg |
|---|---|
| Isomerose | 10 g |
| Mannitol | 5 g |
| Purified water | q.s. |
| Lemon scent | q.s. |

The above ingredients are dissolved in purified water according to a conventional preparation method, and q.s. of lemon scent is added thereto, and then purified water is adjusted to total volume of 100 mL, sterilized and filled in a brown bottle to prepare a liquid formulation.

Preparative Example 6: Preparation of Health Functional Food

| Mixture extract (or extract mixture) | 10 mg |
|---|---|
| Vitamin mixture | q.s. |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | q.s. |
| Ferrous sulfate | 1.75 mg |
| Zinc oxide | 0.82 mg |
| Magnesium carbonate | 25.3 mg |
| Potassium phosphate | 15 mg |
| Dicalcium phosphate | 55 mg |
| Potassium citrate | 90 mg |
| Calcium carbonate | 100 mg |
| Magnesium chloride | 24.8 mg |

The above-mentioned composition ratio of vitamins and minerals is presented in a preferred embodiment based on the relatively suitable ingredients for dietary supplements, but the mixing ratio may be arbitrarily modified. The above ingredients were mixed and granulated according to a conventional preparation method of dietary supplements to use for preparation of the dietary supplement of the present invention.

Preparative Example 7: Preparation of Healthy Beverage

| Scopoletin and rutin | 10 mg |
|---|---|
| Vitamin C | 15 g |
| Vitamin E (powder) | 100 g |
| Ferrous lactate | 19.75 g |
| Zinc oxide | 3.5 g |
| Nicotinamide | 3.5 g |
| Vitamin A | 0.2 g |
| Vitamin B1 | 0.25 g |
| Vitamin B2 | 0.3 g |
| Purified water | q.s. |

The above ingredients are mixed according to a conventional preparation method of healthy beverages and heated with stirring at 85° C. for about 1 hour. The resulting solution is collected by filtration into a sterilized 2 L container, sealed and sterilized, and then stored in a refrigerator to use for preparation of the healthy beverage composition of the present invention.

The above composition ratio is presented in a preferred embodiment based on the relatively suitable ingredients for favorite beverages, but the mixing ratio may be arbitrarily modified according to regional and ethnic preferences such as demand class, demand country, and use purpose.

The above description of the present invention is intended for illustration, and it will be understood by those skilled in the art that it may be easily modified in other specific forms without changing the technical spirit or essential features of the present invention. Therefore, it should be understood the embodiments described above are exemplary in all aspects and not restrictive.

What is claimed is:

1. A method for enhancing immunity, the method comprising consuming an effective concentration of a composition consisting essentially of a mixture extract of goji berry, mulberry, and jujube as an active ingredient in the form of a pharmaceutical composition or in the form of a health functional food to enhance immunity by increasing macrophage-derived TNF-α expression and
   wherein the mixture extract is prepared by
   S1) mixing goji berry, mulberry, and jujube in a weight ratio of about 1:1:0.5;
   S2) adding water to the mixture of step S1) and extracting water at a temperature from about 70° C. to about 100° C.; and
   S3) concentrating the product of step S2) to form a mixture extract.

2. The method for enhancing immunity according to claim 1, further comprising lyophilizing or spray drying the mixture extract and/or mixing an additive with the mixture extract, wherein the additive comprises a carrier, an excipient, a diluent, an extender, a binder, a wetting agent, a disintegrating agent, a surfactant, a lubricant, or a combination thereof.

3. The method for enhancing immunity according to claim 1 comprising administering the pharmaceutical composition at a dose of 0.0001 to 2,000 mg/kg per day.

4. The method for enhancing immunity according to claim 1, wherein the effective concentration is from about 1 μg/ml to about 10 mg/ml.

5. The method for enhancing immunity according to claim 1, wherein the composition further comprises one or more additives selected from a carrier, an excipient, a diluent, an extender, a binder, a wetting agent, a disintegrating agent, a surfactant, or a lubricant.

6. The method of claim 1 wherein the extracting is performed for at least 1 hour.

7. The method of claim 1 wherein the extracting is performed for about 3 hours to about 10 hours and wherein the extracting is performed 2 or 3 times.

8. A method for treating, or ameliorating neurodegenerative diseases, the method comprising consuming an effective concentration of a composition consisting essentially of a mixture extract of goji berry, mulberry, and jujube in the form of a pharmaceutical composition to prevent or treat neurodegenerative diseases or in the form of a health functional food to prevent or ameliorate neurodegenerative diseases, wherein the effective concentration of the composition increases the ratio of mBDNF (mature BDNF) to hippocampal total BDNF and wherein the mixture extract is prepared by
   S1) mixing goji berry, mulberry, and jujube in a weight ratio of about 1:1:0.5;
   S2) adding water to the mixture of step S1) and extracting water at a temperature from about 70° C. to about 100° C.; and
   S3) concentrating the product of step S2) to form a mixture extract.

9. The method for treating, or ameliorating neurodegenerative diseases according to claim 8, further comprising lyophilizing or spray drying the mixture extract and/or mixing an additive with the mixture extract, wherein the additive comprises a carrier, an excipient, a diluent, an extender, a binder, a wetting agent, a disintegrating agent, a surfactant, a lubricant, or a combination thereof.

10. The method for treating, or ameliorating neurodegenerative diseases according to claim 8, wherein the effective concentration is from about 1 μg/ml to about 10 mg/ml.

11. The method for treating, or ameliorating neurodegenerative diseases method according to claim 8, wherein the composition further comprises one or more additives selected from a carrier, an excipient, a diluent, an extender, a binder, a wetting agent, a disintegrating agent, a surfactant, or a lubricant.

12. The method for treating, or ameliorating neurodegenerative diseases according to claim 8, wherein the neurodegenerative disease is Alzheimer's disease.

* * * * *